United States Patent
Kirschman

(10) Patent No.: US 7,566,346 B2
(45) Date of Patent: Jul. 28, 2009

(54) PROSTHETIC IMPLANT AND METHOD

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 739 days.

(21) Appl. No.: 10/976,741

(22) Filed: Oct. 29, 2004

(65) Prior Publication Data

US 2006/0095132 A1 May 4, 2006

(51) Int. Cl.
*A61F 2/44* (2006.01)
(52) U.S. Cl. .............. 623/17.14; 623/17.11; 623/17.15; 623/17.16
(58) Field of Classification Search .............. 623/17.14, 623/17.18, 17.11, 17.15, 23.4, 17.16
See application file for complete search history.

(56) References Cited

U.S. PATENT DOCUMENTS

| | | | |
|---|---|---|---|
| 4,528,990 A | 7/1985 | Knowles | |
| 4,760,851 A | 8/1988 | Fraser et al. | |
| 5,203,346 A | 4/1993 | Fuhr et al. | |
| 5,314,477 A | 5/1994 | Marnay | |
| 5,556,431 A | 9/1996 | Büttner-Janz | |
| 5,582,186 A | 12/1996 | Wiegand | |
| 5,648,296 A | 7/1997 | Salisbury | |
| 5,683,465 A | 11/1997 | Shinn et al. | |
| 5,755,796 A | 5/1998 | Ibo et al. | |
| 5,782,832 A | 7/1998 | Larsen et al. | |
| 5,850,836 A | 12/1998 | Steiger et al. | |
| 5,895,428 A | 4/1999 | Berry | |
| 5,954,674 A | 9/1999 | Fuhr | |
| 6,001,130 A | 12/1999 | Bryan et al. | |
| 6,019,792 A | 2/2000 | Cauthen | |
| 6,063,121 A | 5/2000 | Xavier et al. | |
| 6,113,637 A | 9/2000 | Gill et al. | |
| 6,179,874 B1 | 1/2001 | Cauthen | |
| 6,228,118 B1 | 5/2001 | Gordon | |
| 6,473,717 B1 | 10/2002 | Claussen et al. | |
| 6,540,785 B1 | 4/2003 | Gill et al. | |
| 6,562,045 B2 | 5/2003 | Gil et al. | |
| 6,666,579 B2 | 12/2003 | Jensen | |
| 6,682,562 B2 | 1/2004 | Viart et al. | |
| 6,733,532 B1 | 5/2004 | Gauchet et al. | |
| 6,764,515 B2 | 7/2004 | Ralph et al. | |
| 6,770,095 B2 | 8/2004 | Grinberg et al. | |

(Continued)

FOREIGN PATENT DOCUMENTS

WO    WO 0023015    4/2000

(Continued)

*Primary Examiner*—Corrine M McDermott
*Assistant Examiner*—Rebecca Straszheim
(74) *Attorney, Agent, or Firm*—Jacox, Meckstroth & Jenkins

(57) ABSTRACT

An implant having a first member having a first elongated channel and a second member having a second elongated concave channel that becomes generally opposed when the first and second members are mounted to a first and second vertebra. A ball bearing is received in each of the channels to both separate and maintain a predetermined distance between the first and second member and also to facilitate movement in a plane that intersects an axis of the spinal column. The ball bearing is seated in and cooperates with the channels to permit pivotal movement about a plurality of axes. A method for replacing a disc is also shown using the implant.

10 Claims, 3 Drawing Sheets

U.S. PATENT DOCUMENTS

| | | |
|---|---|---|
| 2003/0055427 A1* | 3/2003 | Graf .......................... 606/61 |
| 2003/0204261 A1* | 10/2003 | Eisermann et al. ....... 623/17.14 |
| 2003/0233146 A1 | 12/2003 | Grinberg et al. |
| 2004/0024462 A1 | 2/2004 | Ferree et al. |
| 2004/0073310 A1 | 4/2004 | Moumene et al. |
| 2004/0093082 A1* | 5/2004 | Ferree ..................... 623/17.11 |
| 2004/0111157 A1 | 6/2004 | Ralph et al. |
| 2004/0133278 A1 | 7/2004 | Marino et al. |
| 2004/0138750 A1* | 7/2004 | Mitchell .................. 623/17.11 |
| 2004/0176844 A1 | 9/2004 | Zubok et al. |

FOREIGN PATENT DOCUMENTS

| | | |
|---|---|---|
| WO | WO 0139678 | 6/2001 |

* cited by examiner

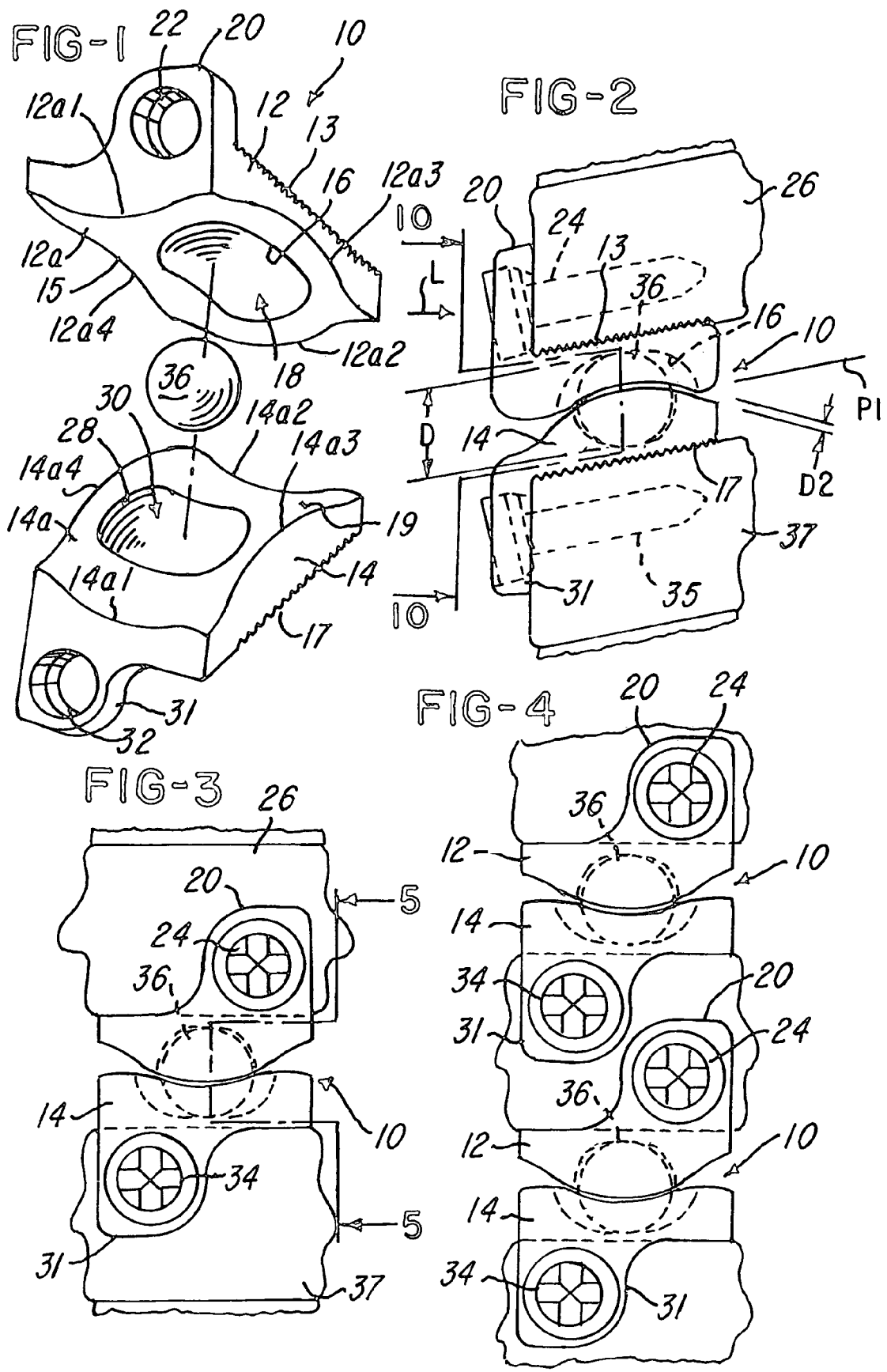

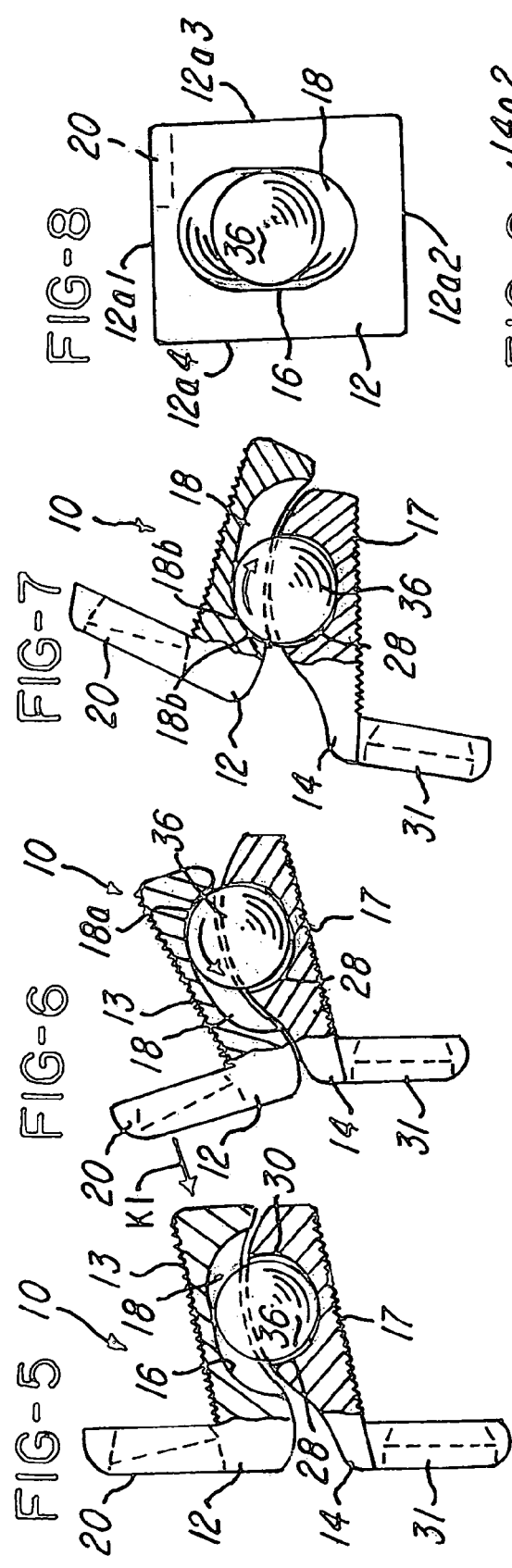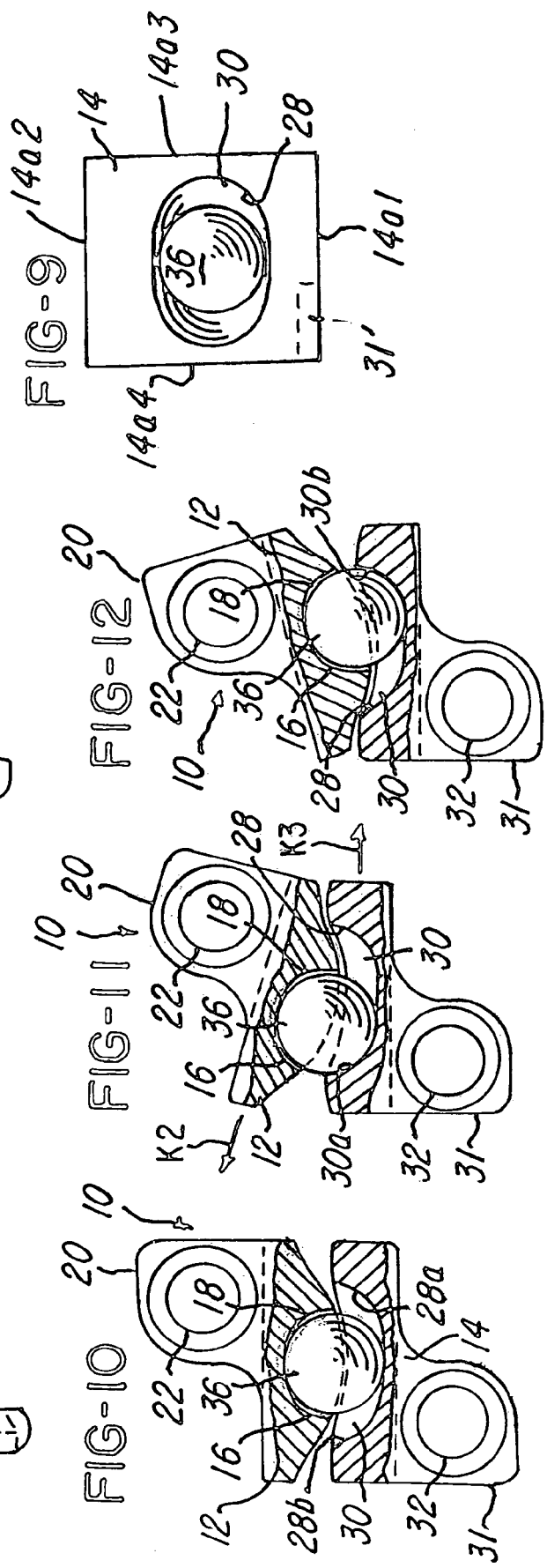

PROSTHETIC IMPLANT AND METHOD

BACKGROUND OF THE INVENTION

The present invention is directed to a prosthesis or implant for use as an intervertebral disc prosthesis having a first member having a first area, groove or channel, a second member having a second area, groove or channel, and a ball bearing for situating in said first and second area, groove or channels.

In cases where intervertebral disc tissue is removed or is otherwise absent from a spinal segment, corrective measures are indicated to insure proper spacing of the vertebrae formally separated by the removed disc tissue. Commonly, the two vertebrae may be fused together using transplanted bone tissue, and artificial fusion element, or other compositions or devices. Unfortunately, spinal fusion has several drawbacks, including preventing the fused vertebrae from moving rotationally or translationally with respect to each other, as natural disc tissue permits. The lack of mobility may increase the stresses on adjacent spinal motion segments.

Several types of inter-vertebral disc arthroplasty devices have been proposed for overcoming some of the problems of the past, and these devices include the devices shown in U.S. Pat. Nos. 4,528,990; 4,760,851; 5,203,346; 5,314,477; 5,556,431; 5,582,186; 5,648,296; 5,683,465; 5,755,796; 5,782,832; 5,850,836; 5,895,428; 5,954,674; 6,001,130; 6,019,792; 6,063,121; 6,113,637; 6,179,874; 6,228,118; 6,473,717; 6,540,785; 6,562,045;. 6,666,579; 6,682,562; 6,733,532; 6,764,515; 6,770,095; and U.S. Publication Nos. 2004/0024462; 2004/0073310; 2004/0111157; 2004/0176844; 2003/0233146; and 2004/0133278.

What is needed therefore is an improved prosthetic implant that overcomes some of the deficiencies of prior designs.

SUMMARY OF THE INVENTION

It is, therefore, an object of the invention to provide a disc replacement implant or prosthesis that supports, preserves and maintains proper disc height, while permitting a close approximation of the physiological function of a disc.

It is another object of the invention to provide an implant that provides proper anatomical motion.

Still another object of the invention is to provide an articulating joint implant that includes first and second members having channels that receive at least one ball bearing.

In one aspect, this invention comprises a prosthesis for situating in a disc area between a first vertebra and a second vertebra, the prosthesis comprising a first member having a first channel area defined by a first channel wall, a second member having a second channel area defined by a second channel wall, and a ball bearing situated in the first and second channel areas, wherein the first and second channel areas are generally perpendicular when the first and second members are mounted to the first and second vertebrae, respectively.

In another aspect, this invention comprises a prosthesis for situating in a disc area between a first vertebra and a second vertebra, the prosthesis comprising a first member having a first channel area defined by a first channel wall, a second member having a second channel area defined by a second channel wall, and a ball bearing situated in the first and second channel areas, wherein the first channel area lies along a radial line extending from a spinal column axis of a spinal column, wherein the second channel area is generally perpendicular to the first channel area.

In still another aspect, this invention comprises a prosthetic implant for use between a first vertebra and a second vertebra, said prosthetic implant comprising a first member comprising a first elongated channel defined by a first channel wall, a second member comprising a second elongated channel defined by a second channel wall, and a ball bearing situated in the first and second elongated channels when the first and second members are mounted to the first and second vertebrae, respectively, the ball bearing permitting relative movement of the first and second members in a first plane and pivotal movement of the first member and the second member about at least one axis, wherein the first and second channel walls comprise a curvature in cross section along their length.

In yet another aspect, this invention comprises a prosthetic implant for use between a first vertebra and a second vertebra, the prosthetic implant comprising a first member comprising a first elongated channel defined by a first channel wall, a second member comprising a second elongated channel defined by a second channel wall, and a ball bearing situated in the first and second elongated channels when the first and second members are mounted to the first and second vertebrae, respectively, the ball bearing permitting relative movement of the first and second members in a first plane and pivotal movement of the first member and the second member about at least one axis, wherein the first and second elongated channels are generally perpendicular when the first and second members are mounted to the first and second vertebrae, respectively.

In another aspect, this invention comprises a prosthetic implant for use between a first vertebra and a second vertebra, the prosthetic implant comprising a first member comprising a first elongated channel defined by a first channel wall, a second member comprising a second elongated channel defined by a second channel wall, and a ball bearing situated in the first and second elongated channels when the first and second members are mounted to the first and second vertebrae, respectively, the ball bearing permitting relative movement of the first and second members in a first plane and pivotal movement of the first member and the second member about at least one axis, wherein the first elongated channel extends in a first direction and the second elongated channel extends in a second direction that is not parallel to the first elongated channel in order to permit relative translational or planar movement of the first and second members.

In still another aspect, this invention comprises a prosthetic implant for use between a first vertebra and a second vertebra, the prosthetic implant comprising a first member comprising a first elongated channel defined by a first channel wall, a second member comprising a second elongated channel defined by a second channel wall, and a ball bearing situated in the first and second elongated channels when the first and second members are mounted to he first and second vertebrae, respectively, the ball bearing permitting relative movement of the first and second members in a first plane and pivotal movement of the first member and the second member about at least one axis, wherein the first and second channel walls are generally perpendicular when said first and second members are mounted to the first and second vertebrae, respectively.

In yet another aspect, this invention comprises an implant comprising a first member for mounting onto a first vertebra, the first member comprising a first channel, a second member for mounting onto a second vertebra, the second member comprising a second channel, and a ball situated in the first and second channels when the first and second members are mounted to the first and second vertebrae, respectively, the first and second channels each comprising a channel width and channel length, the ball having a diameter that is smaller than the channel width of the first and the second channels and the channel length of the first and second channels, the channel width being less than the channel length, wherein the second channel is generally perpendicular to the first channel when the first and second members are mounted to the first and second vertebrae, respectively.

In another aspect, this invention comprises an implant for mounting between a first vertebra and a second vertebra, the implant comprising a first member having a first channel, the first channel comprising a first channel center, a second member having a second channel, the second channel comprising a second channel center, a ball situated in the first and second channels, the first and second channels being dimensioned to permit relative movement of the first and second members in a first plane that is generally perpendicular to a spinal column and pivotal movement between the first member and the second member, wherein the first and second channels are opposed and generally perpendicular when the first and second members mounted on the first and second vertebrae, respectively.

In another aspect, this invention comprises an implant for mounting between a first vertebra and a second vertebra, the implant comprising a first member having a first channel, the first channel comprising a first channel center, a second member having a second channel, the second channel comprising a second channel center, a ball situated in the first and second channels, the first and second channels being dimensioned to permit relative movement of the first and second members in a first plane that is generally perpendicular to a spinal column and pivotal movement between the first member and the second member, wherein both of the first and second channels are concave, wherein the first and second channels are generally perpendicular when the first and second members mounted on the first and second vertebrae, respectively These and other objects and advantages of the invention will be apparent from the following description, the accompanying drawings and the appended claims.

BRIEF DESCRIPTION OF THE DRAWINGS

FIG. 1 is a general perspective and exploded view of an implant or system in accordance with one embodiment of the invention, showing an implant having a first member, a second member and a ball bearing to be received in channels of said first and second members;

FIG. 2 is a side view illustrating the system of FIG. 1 mounted in an inter-vertebral space between a first vertebra and a second vertebra;

FIG. 3 is a view taken in the direction of arrow L in FIG. 2;

FIG. 4 is a view illustrating the use of a plurality of implants in a spinal column;

FIG. 5 is a sectional view taken in the direction of 5-5 in FIG. 3, illustrating the first member and an elongated channel in the first member in an interior-posterior direction and a second member having a second channel with both channels being slightly larger than a diameter of the ball bearing;

FIGS. 6 and 7 are sectional views showing relative pivotal and lateral movement of the first and second members and movement of the ball in the first channel;

FIG. 8 is a diagrammatic bottom view of the top or first member illustrating the ball positioned in the channel;

FIG. 9 is a diagrammatic top view of the second or bottom member shown in FIG. 1 illustrating the ball situated in the second channel;

FIG. 10 is a sectional view taken along the line 10-10 in FIG. 2;

FIGS. 11-12 are sectional views showing the operation of the first and second members and the ball in the second channel, illustrating the relative movement of the first member and the second member;

DETAILED DESCRIPTION

Figure 13:
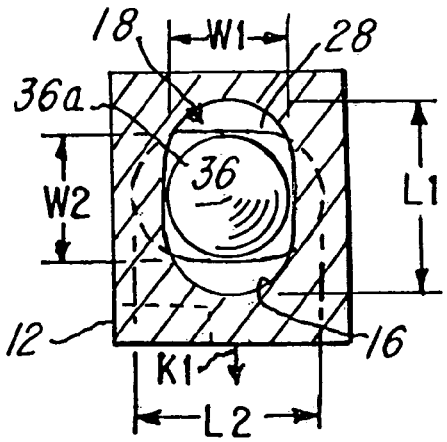
FIG. 13 is a sectional view illustrating the overlapping first and second channels and general perpendicular relationship thereof.

In the following detailed description, for purposes of explanation and not with limitation, examples and embodiments showing specific details are set forth in order to provide a thorough understanding of the present invention. However, it will be apparent to one having ordinary skill in the art having had the benefit of the present disclosure, that the present invention may be practiced in other embodiments that depart from specific details disclosed herein. Moreover, description of well-known apparati and methods may be omitted so as not to obscure the description of the present invention. Such methods and apparati are clearly within the contemplation of the inventor in carrying out the example embodiments. Wherever possible, like numerals refer to like features throughout.

Referring now to FIG. 1, a prosthesis, implant or prosthetic implant 10 is shown. The implant 10 comprises an upper, top, superior or first member 12 and a lower, bottom, inferior or second member 14 as shown. As illustrated in FIG. 1, the first member 12 comprises a first side 13 and a second side or surface 15. The second side 15 comprises channel wall 16 that defines a first concave area, groove or channel 18. In one embodiment, the first channel 18 is elongated and oriented in an anterior-posterior direction, as illustrated in FIGS. 1 and 5-8. The first member 12 also comprises a flange 20 having an aperture 22 for receiving a screw, such as screw 24 in FIG. 2, for mounting the first member 12 onto a first vertebra 26.

The implant 10 further comprises the bottom member 14 having a first side 17 and second side 19. The second side or surface 19 comprises a channel wall 28 that defines a second concave elongated area, groove or channel 30 as shown. The channel walls 16 and 28 are curved in cross-section along their length and width. As with the first member 12, the second member 14 also comprises a flange 31 having an aperture 32 for receiving a screw 35 (FIG. 2) for mounting the second member 14 onto a second vertebra 37. Note the flanges 20 and 31 are angled such that the surfaces 15 and 19 lay in a correct anatomical plane relative to vertebrae 26 and 37 and the spinal column. As illustrated in FIGS. 1 and 9-12, the second channel 30 is situated in a generally perpendicular relationship relative to the first channel 18, as illustrated in FIGS. 8, 9 and 13. Note that the first side 13 and 17 may be serrated to facilitate a snug and secure engagement against the vertebrae 26 and 37, respectively.

Referring back to FIG. 1, notice that the implant 10 further comprises a ball or ball bearing 36 which becomes situated in the channels 18 and 30, as illustrated in FIGS. 2-4. The bearing 36 provides support between the first and second members 12 and 14 and facilitates not only maintaining a predetermined distance D (FIG. 2), which generally corresponds to a diameter of the ball 36, but also enables the first and second members 12 and 14 to move in a plane, such as plane P1 in FIG. 2, that intersects a spinal cord axis (not shown) of a spinal cord (not shown). As is described later herein, the first and second members 12 and 14 can also pivot about at least one or a plurality of axes. The operation and function of the first and second members 12 and 14 and their associated channels 18 and 30 and ball 36 is described later herein.

FIG. 2 illustrates the implant 10 mounted between the first vertebra 26 and second vertebra 37 as shown. Note that the elongated first channel 18 becomes situated along a radial line extending from a spinal column axis along its longitude, and the second channel 30 has a longitude that is generally perpendicular to the first channel 18 when the first member 12 is mounted to vertebra 26 and second member 14 is mounted to vertebra 37. This generally perpendicular relationship is illustrated in FIGS. 8-13. In the illustration being described, the first member 12 comprises a first length L1 and a first width W1 which is less than the first length L1, as illustrated in FIG. 13. Likewise, the channel 30 of the second member 14 comprises a width W2 and a length L2, with the length L2 being greater than the width W2. In one embodiment, the widths W1 and W2 generally correspond and lengths L1 and L2 also generally correspond. Notice the cross-sectional widths W1 and W2 (FIG. 13) of the channels 18 and 30 have a radius of curvature and are slightly larger than the diameter of the ball 36 in order to permit the ball 36 to roll, slide or rotate within the channels 18 and 30 and also to reduce the friction between the outer surface 36a of ball 36 and the inner walls 16 and 28. Also, the ball 36 comprises a diameter which is slightly smaller than the widths W1 and W2 so that the ball 36 can rotate or slide and move freely in the channels 18 and 30. It should be understood that the ball 36 is dimensioned and comprises a diameter that is selected to maintain a predetermined distance, such as distance D2 in FIG. 2, between the surfaces 15 and 19 and first member 12 and second member 14, respectively. In the embodiment being described, the ball 36 comprises a diameter that is on the order of about 6 mm. Likewise, the widths W1 and W2 are on the order of about 6 mm, while the lengths L1 and L2 are on the order of about 12 mm. It should be appreciated that the widths W1 and W2 and lengths L1 and L2 mentioned herein are illustrative and other dimensions may be selected if desired.

The interior surface 12a of first member 12 and interior surface 14a of second member 14 are generally curved or even saddle-shaped to permit the vertebra 26 and 37 to articulate or move in the manner illustrated in FIGS. 5-7 and 10-12, without the surfaces 15 and 19 engaging during such movement.

In the embodiment being described, the first and second members 12 and 14 are capable of movement (such as non-pivotal, lateral or translational movement) in the plane P1 (FIG. 2) and are also capable of movement about at least one or a plurality of axes which will now be described relative to FIGS. 14-16. In the illustration shown in FIGS. 14-16, two imaginary points A and B are identified for ease of understanding the pivotal movement of the members 12 and 14 about the multiple axes. Note that the channel wall 16 defines the elongated channel 18 which in turn defines a curvature having at least one radius of curvature R1 as shown. The radius of curvature R1 comprises a center axis C1 about which the first member 12 may pivot. Likewise, the second member 14 comprises a curvature having at least one second radius of curvature R2 associated with channel wall 28 and defining a second center or axis of rotation C2, as illustrated in FIG. 15. The ball 36 comprises a surface 36a comprising a third radius of curvature R3 that defines an axis center C3 about which the first and second members 12 and 14 may rotate. The channels 18 and 30 also have curvatures in cross-sectional having radii of curvature defined by the cross-sectional curved shape of walls 16 and 28, respectively. These radii of curvature are smaller than the radii of curvature of R1 and R2.

The first and second members 12 and 14 and their associated channels 18 and 30 may roll on, slide across and/or pivot about the ball 36, thereby enabling the first and second members to pivot about ball axis C3, as well as or more of the axes or centers of rotation C1-C2. For example, as illustrated in FIGS. 5-7 and 16, the ball 36 permits the first member 12 and second member 14 to move relative to each other in the plane P1 (FIG. 2), such as in relative lateral or translational direction. Thus, the first member 12 may move in a forward direction or in the direction of arrow K1 (FIG. 6), whereupon the ball 36 becomes positioned at an end 18a of channel 18, as illustrated in FIG. 6. Relative movement between first member 12 and second member 14, such as if first member 12 moves in a direction opposite of arrow K1, enables the ball 36 to be positioned at an opposite end 18b of channel 18, as shown in FIG. 7. Similarly, the first member 12 and second member 14 may have the relative movement illustrated in FIGS. 10-12 where, as a result of movement between members 12 and 14, the ball 36 becomes positioned, for example, from a generally central position in channel 30 (FIG. 10) to a position where the ball 36 becomes situated at an end 30a of channel 30, as shown in FIG. 11. When there is relative movement between the first and second members 12 and 14, such as when the first member 12 moves in a direction of arrow K2 (FIG. 11) and/or the bottom member 14 moves in the direction of arrow K3, the ball 36 becomes positioned at another end 30b of channel 30 which is illustrated in FIG. 12.

Thus, it should be appreciated that the first and second members 12 and 14 may pivot or move along the first and second walls 16 and 28 such that points A and B move along a curve or arc 50 (FIGS. 5, 15 and 16) that is directly related to the curvature defined by the first radius of curvature R1 for first member 12 and the curvature defined by the second radius of curvature R2. This pivotal movement is generally defined by the central portion 16c and 28c of walls 16 and 28, respectively, (FIG. 1) and about respective centers C1 and C2, respectively, when the ball 36 moves along the longitudinal length of the channels 18 and 30. Thus, as illustrated in FIGS. 5-7, described earlier herein, the ball 36 may move along the longitudinal direction of the channel 18 as illustrated, and substantially simultaneously, or even independently, the second member 14 may pivot about the axis C3 of ball 36. The first member 12 may also pivot about the axis C3 of ball 36 (as illustrated in FIGS. 10-12) either before, during or after the first member 12 and the second member 14 have moved relative to each other and/or pivoted about the axes C1 and C2, respectively.

Thus, each member 12 and 14 is also capable of pivotal movement about ball axis C3. In this case, the points A and B (FIGS. 14-16) move along a curve or arc 52 that is directly related to the curvature associated with the radius of curvature of ball 36. Thus, for example, as the ball 36 moves in the channel 30 of the second member 14 in the manner shown in FIGS. 10-12, the second member 14 may pivot about the axis C2 (FIG. 15) associated with radius of curvature R2 and also about ball axis C3. Again, substantially simultaneously or even independently, the first member 12 and/or second member 14 may pivot about axes C1 and C2, respectively, and about the axis C3 of ball 36. Accordingly, it should be appreciated that each of the members 12 and 14 cooperate with ball 36 to enable universal movement of the members 12 and 14 in the plane P1 (FIG. 2) and further permitting pivotal movement about at leas tone or multiple axes, thereby providing a full range of relative movement between the first and second members 12 and 14 that further permits the vertebrae 26 and 37 to exactly or closely approximate normal physiologic range of motion.

As mentioned earlier, the ball 36 is dimensioned to rotate and/or slide in the channels 18 and 30. After the first member 12 is secured to the vertebra 26 with the screw 24 and second member 14 is secured to the vertebra 37 with screw 34, the longitude or length of channel 18 is situated relative to a spinal column (not shown) along its longitude such that the channel 30 becomes situated in plane P1 and lies along a radial line extending from the spinal column axis (not shown). The second channel 30 is perpendicular to channel 18. This generally perpendicular relationship is illustrated in the diagrammatic view shown in FIG. 13. This facilitates the first member 12 and second member 14 to move generally universally in the plane P1 in the manner described herein. Thus, forward or anterior-posterior movement of the first member 12 is assigned to the first member 12, while lateral or relative lateral movement between the first vertebra 26 and second vertebra is assigned to the lower or second member 14.

As alluded to earlier herein, the ball 36 may pivot or roll in one of the axes or channels 18 and 30 while sliding in another axis or channel 30 and 18. Thus, for example, the ball 36 may roll along the channel wall surface 16 of first member 12, while rolling or sliding against or across the channel wall surface 28 within second channel 30 as the ball 36 rolls in the first channel 18. Likewise, the ball 36 may roll along channel wall surface 28 in the longitudinal direction of channel 30, while sliding or rolling against or across the cross-sectional width of the wall 16 within channel 18. Thus, not only does the implant 10 provide for generally universal relative movement of the first and second members 12 and 14 in the plane P1 (FIG. 2), one or both of the members 12 and 14 may substantially simultaneously or independently pivot about the axis C3 and/or about their respective axes C1 and C2 described earlier.

The channel walls 16 and 28 may define a curvature that is not constant to facilitate retaining the ball 36 in the channel. For example, as best illustrated in FIG. 16, note that the first member 12 comprises the channel wall 16 having end portions 16a and 16b that define a fourth radius of curvature R4 about a fourth center or axis C4 and a fifth radius of curvature R5 about a fifth center or axis C5. Note that the radii of curvatures R4 and R5 are smaller than the radius of curvature of a central portion 16c of wall 16. This facilitates retaining the ball 36 in the channel 18 when the ball 36 reaches the ends 16a and 16b of the wall 16 defining channel 18, as illustrated in FIGS. 6 and 7 described earlier herein. Likewise, the wall 28 comprises ends 28a and 28b that have curvatures having radii of curvature R6 and R7 that are smaller than the radius of curvature R2 to facilitate retaining the ball in the channel 30 when the ball reaches the ends 30a as illustrated in FIGS. 11 and 12. Although not shown, less than all of the ends 16a, 16b and 28a and 28b may have the smaller radii of curvature if desired.

Figure 14:
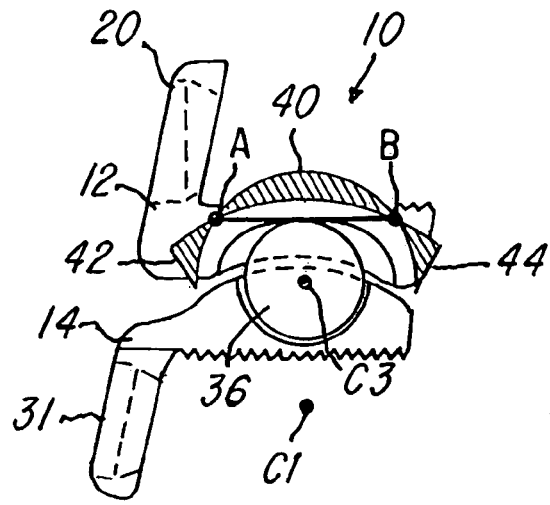
FIG. 14 is a view similar to FIG. 2, without showing the vertebrae, and illustrating a zone of pivotal movement defined by a generally crescent-shaped region having a crescent-shaped portion which illustrates pivotal movement about a plurality of axes.
Figure 15:
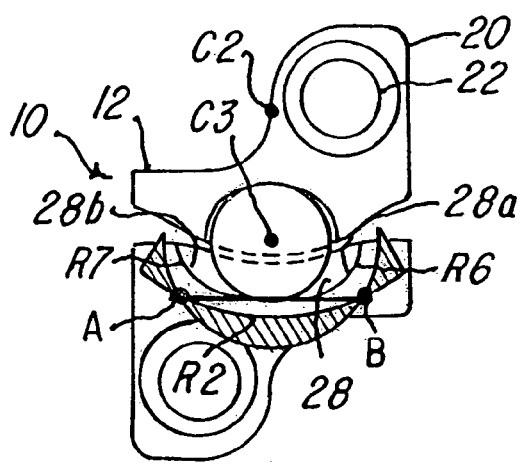
FIG. 15 is a view similar to FIG. 14 showing a region or area of movement for ease of illustrating pivotal movement of the lower or second member about a plurality of axes.
Figure 16:
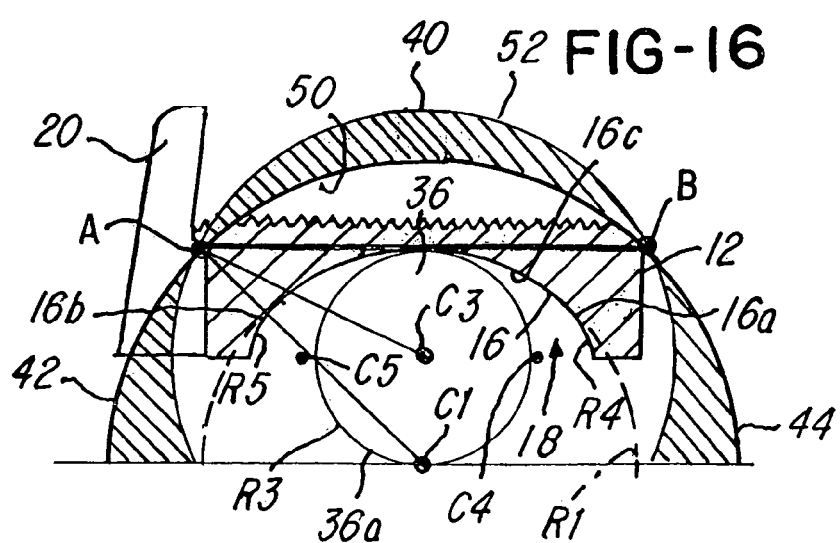
FIG. 16 is an enlarged view of the first member and ball shown in FIG. 14 further illustrating a plurality of radii of curvature and the pivotal movement about a plurality of axes and illustrating one possible area

As illustrated in FIGS. 14-16, the movement about the centers or axes (such as axes C1, C2 and C3 in FIGS. 15 and 16) enables the members 12 and 14 to move within the crescent-shaped zone area 40 and zone areas 42 and 44, depending on whether the first and second members 12 and 14 are moving about the axis C1, C2, C3, or any point within an infinite range of points therebetween. In any event, the channels 18 and 30 and the arrangement of the channels 18 and 30 when the first and second members 12 and 14 are mounted on the vertebrae 26 and 37, respectively, enable the first and second members 12 and 14 to move within the areas 40, 42 and 44 whose boundaries in one or more embodiment are defined by arcs or curves 50 and 52 which is diagrammatically illustrated by the areas 40, 42 and 44. The movement of the upper member 12 with respect to the lower member 14 is centered upon multiple and variable axes of rotation, highly conforming to the multiple external forces placed upon the device by the natural motions of the spine. It should be understood that FIGS. 14-16 is merely illustrative of the zones of movement when the first and second members 12 and 14 are shown in the positions relative to the ball 36. Other zones (not shown) are realized when the position of the ball 36 changes relative to the first and second members 12 and 14.

During a surgical procedure, a method for replacing a disc (not shown) may comprise the steps of mounting the first member 12 to the first vertebra 26, mounting the second member 14 to the second vertebra 37 while situating, or causing to be situated, the ball 36 within the channels 18 and 30. The channels 18 and 30 are dimensioned and provided in the shape and configuration shown to provide universal relative movement of the first and second members 12 and 14 in the plane P1 and pivotal movement about at least one or a plurality of axes, such as the axis C3, axis C1 or axis C2. Thus, the first and second channels 18 and 30 may also be dimensioned to not only permit relative movement of the first and second members 12 and 14 in the plane P1, but also permit pivotal movement about the plurality of axes as described earlier herein.

In accordance with illustrative embodiments, methods and apparati have been described for facilitating maintaining a distance D1 in FIG. 2 between the first vertebra 26 and second vertebra 37 while substantially simultaneously permitting normal physiological movement between the vertebrae 26 and 37. As illustrated in FIGS. 2 and 3, the implant 10 may be used in a spinal column between two vertebrae 26 and 37, but it is also envisioned that multiple implants 10 may be used in a single spinal column, as illustrated in FIG. 4. In certain embodiments, the channels 18 and 30 are shown in perpendicular relationship as illustrated in FIGS. 8, 9 and 13, but the first and second members 12 and 14 may comprise channels 18 and 30 that are arranged in other than a perpendicular arrangement without departing from the true spirit and scope of the invention. Also, although the preferred embodiment shows use of a single ball 36, one or more other balls (not shown) having the same or a different diameter. The illustrations described, show each member having one channel, but more channels could be used. Although not shown, it is also envisioned that one channel provided in only one of the members 12 and 14 may be provided.

In the embodiment being described, the members 12, 14 and ball 36 may be made of cobalt alloy, polyethylene, ceramic, cobalt-chrome that is polished to provide a smooth bearing surface, stainless steel and/or titanium, ceramic materials (e.g., alumina and zirconium), or any other suitable material. The screws 24 and 34 are held in place via frictional forces between the screw head and screw socket. Alternatively, the device can be provided with no screws, the device being held in place by frictional forces between the device and disk space.

The various implants, methods, materials, components and parameters are included by way of example only and not in any limiting sense. Therefore, the embodiments described herein are illustrative and are useful in providing, inter alia, beneficial articulating joint for use in a patient. In view of this disclosure, those skilled in the art can implement the various example apparati and methods to affect these and other assemblies, while remaining within the true spirit of the scope of the appended claims.

What is claimed is:

1. A prosthesis for situating in a disc area between a first vertebra and a second vertebra, said prosthesis comprising:
   a first member having a first channel defined by a first channel wall;
   a second member having a second channel defined by a second channel wall; said first and second channels each comprising a length and a width, said length being greater than said width; and
   a ball bearing situated in and adapted to roll in said first and second channels, said ball bearing having a spherical shape;
   wherein said length of said first channel is generally perpendicular to said length of said second channel when said first and second members are mounted to said first and second vertebrae, respectively.

2. A prosthesis for situating in a disc area between a first vertebra and a second vertebra, said prosthesis comprising:
   a first member having a first channel defined by a first channel wall;
   a second member having a second channel defined by a second channel wall; each of said first and said second channels comprising a length and a width, said length being greater than said width; and
   a ball bearing situated in and adapted to roll in said first and second channel, said ball bearing having a spherical shape;
   wherein said first channel lies along a radial line extending from a spinal column axis of a spinal column;
   wherein said length of said second channel is generally perpendicular to said length of said first channel.

3. A prosthetic implant for use between a first vertebra and a second vertebra, said prosthetic implant comprising:
   a first member comprising a first elongated channel defined by a first channel wall;
   a second member comprising a second elongated channel defined by a second channel wall; each of said first and second elongated channels comprising a length and a width, said length being greater than said width; and
   a ball bearing situated in said first and second elongated channels when said first and second members are mounted to said first and second vertebrae, respectively, said ball bearing having a spherical shape;
   said ball bearing adapted to roll in said first and second elongated channels to permit relative movement of said first and second members in a first plane and pivotal movement of said first member and said second member about at least one axis;
   wherein said length of said first channel wall is generally perpendicular to said length of said second channel wall and comprise a curvature in cross section along their length.

4. A prosthetic implant for use between a first vertebra and a second vertebra, said prosthetic implant comprising:
   a first member comprising a first elongated channel defined by a first channel wall;
   a second member comprising a second elongated channel defined by a second channel wall; each of said first and second elongated channels comprising a length and a width, said length being greater than said width; and
   a ball bearing situated in said first and second elongated channels when said first and second members are mounted to said first and second vertebrae, respectively, said ball bearing having a spherical shape;
   said ball bearing adapted to roll in said first and second elongated channels to permit relative movement of said first and second members in a first plane and pivotal movement of said first member and said second member about at least one axis;
   wherein said length of said first elongated channel is generally perpendicular to said length of said second elongated channel when said first and second members are mounted to said first and second vertebrae, respectively.

5. A prosthetic implant for use between a first vertebra and a second vertebra, said prosthetic implant comprising:
   a first member comprising a first elongated channel defined by a first channel wall;
   a second member comprising a second elongated channel defined by a second channel wall; each of said first and second elongated channels comprising a length and a width, said length being greater than said width; and
   a ball bearing situated in said first and second elongated channels when said first and second members are mounted to said first and second vertebrae, respectively, said ball bearing having a spherical shape;
   said ball bearing adapted to roll in said first and second elongated channels to permit relative movement of said first and second members in a first plane and pivotal movement of said first member and said second member about at least one axis;
   wherein said length of said first elongated channel is generally perpendicular to said length of said second elongated channel in order to permit relative translational or planar movement of said first and second members.

6. A prosthetic implant for use between a first vertebra and a second vertebra, said prosthetic implant comprising:
   a first member comprising a first elongated channel defined by a first channel wall;
   a second member comprising a second elongated channel defined by a second channel wall; said first and second elongated channels each comprising a length and a width, said length being greater than said width; and
   a ball bearing situated in said first and second elongated channels when said first and second members are mounted to said first and second vertebrae, respectively, said ball bearing having a spherical shape;
   said ball bearing adapted to roll in said first and second elongated channels to permit relative movement of said first and second members in a first plane and pivotal movement of said first member and said second member about at least one axis;
   wherein said length of said first elongated channel is generally perpendicular to said length of said elongated second channel when said first and second members are mounted to said first and second vertebrae, respectively.

7. An implant comprising:
   a first member for mounting onto a first vertebra, said first member comprising a first channel;
   a second member for mounting onto a second vertebra, said second member comprising a second channel; and
   a ball situated in said first and second channels when said first and second members are mounted to said first and second vertebrae, respectively;
   said first and second channels each comprising a channel width and a channel length;
   said ball having a diameter that is smaller than said channel width of said first and said second channels and said channel length of said first and second channels, said channel width being less than said channel length, said ball having a spherical shape and adapted to roll in said first and second channels;

wherein said length of said second channel is generally perpendicular to said length of said first channel when said first and second members are mounted to said first and second vertebrae, respectively.

8. The implant as recited in 7 wherein said first channel extends along a radial line associated with a spinal column axis of a spinal column.

9. An implant for mounting between a first vertebra and a second vertebra, said implant comprising:

a first member having a first channel, said first channel comprising a first channel center;

a second member having a second channel, said second channel comprising a second channel center; said first and second channels comprising a length and a width, said length being greater than said width; and a ball situated in and adapted to roll in said first and second channels, said ball having a spherical shape;

said first and second channels being dimensioned to permit relative movement of said first and second members in a first plane that is generally perpendicular to a spinal column and pivotal movement between said first member and said second member;

wherein said length of said first channel is generally perpendicular to said channel of said second channel when said first and second members mounted on said first and second vertebrae, respectively.

10. An implant for mounting between a first vertebra and a second vertebra, said implant comprising:

a first member having a first channel, said first channel comprising a first channel center;

a second member having a second channel, said second channel comprising a second channel center; said first and second channels comprising a length and a width, said length being greater than said width; and a ball situated in and adapted to roll in said first and second channels, said ball having a spherical shape;

said first and second channels being dimensioned to permit relative movement of said first and second members in a first plane that is generally perpendicular to a spinal column and pivotal movement between said first member and said second member;

wherein both of said first and second channels are concave;

wherein said length of said first channel is generally perpendicular to said length of said second channel when said first and second members mounted on said first and second vertebrae, respectively.

* * * * *

UNITED STATES PATENT AND TRADEMARK OFFICE
CERTIFICATE OF CORRECTION

| | | |
|---|---|---|
| PATENT NO. | : 7,566,346 B2 | Page 1 of 1 |
| APPLICATION NO. | : 10/976741 | |
| DATED | : July 28, 2009 | |
| INVENTOR(S) | : David Louis Kirschman | |

It is certified that error appears in the above-identified patent and that said Letters Patent is hereby corrected as shown below:

In Column 1, Line 22, please delete "inter-vertebral" and insert --intervertebral-- therefor.

In Column 2, Line 50, please delete "he" and insert --the-- therefor.

In Column 3, Line 47, please delete "inter-vertebral" and insert --intervertebral-- therefor.

In Column 7, Line 7, please delete "leas tone" and insert --least one-- therefor.

Signed and Sealed this
Fifth Day of April, 2011

David J. Kappos
*Director of the United States Patent and Trademark Office*